United States Patent [19]
Ferrari et al.

[11] Patent Number: 5,886,002
[45] Date of Patent: Mar. 23, 1999

[54] USE OF RIFAXIMIN AND OF PHARMACEUTICAL COMPOSITIONS CONTAINING IT IN THE TREATMENT OF THE DIARRHOEA FROM CRYPTOSPORIDIOSIS

[75] Inventors: Patrizio Ferrari; Antonella Ferrieri, both of Bologna; Pietro Caramello, Turin, all of Italy

[73] Assignee: Alfa Wassermann S.p.A., Alanno, Italy

[21] Appl. No.: 13,655

[22] Filed: Jan. 26, 1998

[30] Foreign Application Priority Data

Feb. 14, 1997 [IT] Italy .................................. B097A0064

[51] Int. Cl.$^6$ ..................................................... A61K 31/44
[52] U.S. Cl. ........................... 514/279; 514/394; 514/867
[58] Field of Search ..................................... 514/867, 279, 514/394

[56] References Cited

U.S. PATENT DOCUMENTS 5,352,679  10/1994  Ferrari et al. ............................ 514/279

*Primary Examiner*—Frederick Krass
*Attorney, Agent, or Firm*—Bucknam and Archer

[57] ABSTRACT

The use of therapeutically effective amounts of rifaxmin and of pharmaceutical compositions containing it in the treatment of the diarrhoeal symptomatology in case of cryptosporidiosis in patients suffering from severe forms of immunodepression, for instance patients suffering from AIDS or malignant neoplasias, or subjected to transplantations or treated with chemotherapeutic or immunosuppressive agents is the object of the present invention.

3 Claims, No Drawings

USE OF RIFAXIMIN AND OF PHARMACEUTICAL COMPOSITIONS CONTAINING IT IN THE TREATMENT OF THE DIARRHOEA FROM CRYPTOSPORIDIOSIS

BACKGROUND OF THE INVENTION

The *Cryptosporidium parvum* is a protozoan responsible for an oro-fecal transmitted zoonosis which until about 20 years ago was of sole veterinary interest.

Following the recent coming of the immune deficiency syndromes, mainly from HIV infections, and the increase of the treatments which cause immnunodepression in patients suffering from malignant neoplasias or submitted to organs' transplantation, an increasing diffusion of diarrhoeal events with long duration, sometimes many weeks, and of severe seriousness has occurred as reported by Meisel J. L. et al., Gastroenterology, 70, 1156–1160, (1976) and by Current W. L. and Garcia L. S., Clin. Microbiol. Rev., 4, 325–358, (1991).

Epidemiological studies carried out by Laughon B. E. et al., Gastroenterology, 94, 984–993, (1988) and by Colbunders R. et al., Am. J. Gastroenterol., 82, 859–864, (1987) on patients suffering from acquired immune deficiency syndrome (AIDS) showed that the frequency of the diarrhoea from cryptosporidiosis reaches the 10–15% of the patients suffering from AIDS in the United States to raise until 30–50% of the same persons in the developing countries.

The mechanism that causes the diarrhoeal infection is not well known; Bonnin A. and Camerlynck P., Encycl. Med. Chir. (Paris-France), Maladies Infectieuses, 8, 501–10, (1992) think toxins cholera-like that directly act on the adenylate-cyclase system of the intestinal epithelium or a secondary alteration of the villi, responsible of the passing of undigested disaccharides through the large intestine with subsequent osmotic diarrhoea, are responsible for the unleashing of the severe diarrhoeal symptomatology in patients suffering from AIDS.

The infection from *Cryptosporidium parvum*, after a period of incubation of about a week, in the patients suffering from AIDS appears in the shape of an aqueous profuse diarrhoea joined to strong abdominal pains, vomit, fever, cephalea and asthenia. This severe diarrhoeal form lasts for several weeks and causes severe hydroelectrolitic unbalances, dehydratation, malnutrition, renal insufficiency and, sometimes, bronchopulmonary complications in the organism already strongly weakened.

Petersen C., Clin. Infect. Dis., 15, 903–909, (1992) and Goodgame R. W. et al., J. Infect. Dis, 167, 704–709, (1993) showed a close relationship between the degree of seriousness and duration of this kind of diarrhoeal form and the degree of immunodepression: the spontaneous remission of the diarrhoeal events is observed within a month from the beginning in the patients suffering from AIDS in whom the CD4 values are yet more than 200 mm$^3$, while the diarrhoeal pathology becomes chronic together with frequent appearance of complications in the more severe cases of immunodepression, with CD4 values lower than 100 mm$^3$.

At present a well-established therapy of the diarrhoea from cryptosporidiosis linked to the acquired immune deficiency syndrome (AIDS) does not exist yet even if some authors reported partial results with some types of drugs. Portnoy D. et al., Ann. Intern. Med., 101, 202–204, (1984) and Connolly G. M. et al., Gut, 29, 593–597, (1988) reported initial positive results with the spiramycin, results that have not been subsequently confirmed by Wittenberg D. F. et al., J. Infect. Dis., 159, 131–132, (1989).

White A. C. Jr. et al., J. Infect. Dis., 170, 419–424, (1994) and Walmsley S. et al., *Program and abstracts: IX International Conference on AIDS/IV STD World Congress* (Berlin). London: Wellcome Foundation, (1993) reported significant clinical and parasitologic improvements with a treatment based on an administration of 2 g a day of paramomicin for two or more weeks, but any parasitologic eradication has not been obtained as showed in the 58% of recidivations.

Finally Vargas S. L. et al., J. Pediatr., 123, 154–156, (1993) and Dunne M. W., *Program and abstracts: IX International Conference on AIDS/IV STD World Congress* (Berlin). London: Wellcome Foundation, (1993) showed initial effectiveness proofs by using high doses of azitromycin.

DESCRIPTION OF THE INVENTION

The use of therapeutically effective amounts of rifaximin and of pharmaceutical compositions containing it, orally administrable, in the treatment of the diarrhoea from cryptosporidiosis in patients suffering from severe forms of immunodepression, mainly in patients suffering from AIDS or malignant neoplasias, or subjected to transplantations or treated with chemotherapeutic or immunosuppressive agents, is the object of the present invention.

Rifaxiiin is an antibiotic discovered in 1980 and patented in Italy, IT Patent 1154655 granted on Jan. 21, 1987, an in many other countries, active against many types of bacteria both gram-positive and gram-negative. It is marketed in Italy since 1985 under the trademark NORMIX® for treating acute and chronic intestinal infections from gram-positive and gram-negative bacteria and as adjuvant in the therapy of the hyperammonoaemia.

At present NORMIX® is marketed in the shape of pharmaceutical compositions, orally administrable, made by tablets or by granulates containing suitable pharmaceutically acceptable excipients together with rifaximnin, but also other pharmaceutical forms orally administrable like capsules, sugar coated tablets and syrups can be advantageously used in carrying out the present invention.

At present rifaximin has been studied and marketed only for the treatment of some kinds of bacterial infections and any possible antiprotozoal activity or any possible use as antiprotozoal drug has never been investigated.

Our researchers have now discovered that this antibiotic possesses also antiprotozoal activity against the *Cryptosporidium parvum* protozoan and that its administration at daily doses between 1200 and 2400 mg for a period of time between 1 and 4 weeks causes the parasitologic eradication and the disappearance of the diarrhoeal phenomena linked to cryptosporidiosis infection in immunodepressed patients.

The diagnosis of cryptosporidiosis has been made on the basis of the identification of the *Cryptosporidium parvum* in the feces by means of examination with the optical microscope and of immunoenzymatic test (ELISA).

The treatment of patients suffering from AIDS and affected by diarrhoeal symptomatology from cryptosporidiosis with from 1200 to 2400 mg a day of rifaximin contained into 200 mg tablets in the medicine NORMIX® for a period of time between 1 and 4 weeks has been positive causing a clear-cut improvement of the clinical picture in about 80% of the treated patients and the lack in the feces of the oocysts of *Cryptosporidium parvum* in about 60% of the cases at the end of the treatment.

All the clinical parameters resulted to be clearly improved at the end of the treatment attesting the effectiveness of the use of rifaximin. The example concerning the under reported clinical test has to be considered as a further illustration of the invention and not as an its limitation.

EXAMPLE 1

Twelve patients, 8 men and 4 women aged between 29 and 51 years, suffering from AIDS and affected by secondary diarrhoea caused by infection from *Cryptosporidium parvum* have been enrolled at some Divisions of Infectivology of the Piedmont Region co-ordinated by the Institute of Infective Diseases of the Turin University. All the enrolled patients showed a very strong immunodepression with CD4 values lower than 50 $mm^3$ and diarrhoeal symptoms present on the average from 13 days before the beginning of the treatment.

The clinical diagnosis of infection from *Cryptosporidium parvum* has been confirmed by means of parasitologic examination of the feces with the electronic microscope and by means of immunoenzymatic test (ELISA).

Three NORMIX® tablets, each containing 200 mg of rifaximin, have been orally administered to the patients three times a day, totalling 1800 mg a day of rifaximin, for an average period of 14 days, from a minimum of 10 days to a maximum of 21 days.

At the end of the treatment, the parasitologic examination of the feces showed the disappearance of the oocysts of *Cryptosporidium parvum* in 7 out of 12 patients. Four patients got the disappearance of the whole diarrhoeal symptomatology while 6 patients got a clear improvement of the clinical picture with a strong decrease of the alvine discharges and modification of the type of the feces from soft or watery to well-built; only 2 patients did not favourably respond to the treatment.

No patient showed adverse effects due to the rifaximin treatment and the dosage has never been reduced nor the treatment has been broken off.

We claim:

1. A method of treatment of the diarrhoea from cryptosporidiosis which consists of administering orally to a subject in need of such treatment a pharmaceutical composition containing a therapeutically effective amount of rifaximin.

2. A method according to claim 1 wherein said pharmaceutical composition is selected from tablets, capsules, sugar coated tablets, granulates or syrups.

3. A method according to claim 1 wherein said therapeutically effective amount of rifaximin is between 1200 and 2400 mg a day.

\* \* \* \* \*